(12) United States Patent
Takahashi et al.

(10) Patent No.: US 9,822,061 B2
(45) Date of Patent: Nov. 21, 2017

(54) METHOD FOR PRODUCING NITRO COMPOUND

(71) Applicant: SUMITOMO CHEMICAL COMPANY, LIMITED, Tokyo (JP)

(72) Inventors: Teruki Takahashi, Takarazuka (JP); Kazuya Ueki, Takarazuka (JP); Yuta Nagashima, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/300,010

(22) PCT Filed: Apr. 8, 2015

(86) PCT No.: PCT/JP2015/061526
§ 371 (c)(1),
(2) Date: Sep. 28, 2016

(87) PCT Pub. No.: WO2015/159904
PCT Pub. Date: Oct. 22, 2015

(65) Prior Publication Data
US 2017/0144961 A1    May 25, 2017

(30) Foreign Application Priority Data

Apr. 17, 2014 (JP) .................. 2014-085244

(51) Int. Cl.
C07C 201/12 (2006.01)
C07C 205/11 (2006.01)
C07C 209/68 (2006.01)

(52) U.S. Cl.
CPC .......... C07C 201/12 (2013.01); C07C 205/11 (2013.01); C07C 209/68 (2013.01)

(58) Field of Classification Search
CPC .... C07C 201/12; C07C 205/11; C07C 209/68
See application file for complete search history.

(56) References Cited

U.S. PATENT DOCUMENTS

2004/0199002 A1   10/2004   Abe et al.

FOREIGN PATENT DOCUMENTS

JP     60-25957 A      2/1985
JP     2003-171359 A   6/2003
(Continued)

OTHER PUBLICATIONS

Makosza et al., Dihalomethylation of nitroarenes, (Journal of Organic Chemistry, 1989, 54, 5094-5100).*

(Continued)

*Primary Examiner* — Jafar Parsa
(74) *Attorney, Agent, or Firm* — Birch, Stewart, Kolasch & Birch, LLP

(57) ABSTRACT

A compound represented by formula (1):

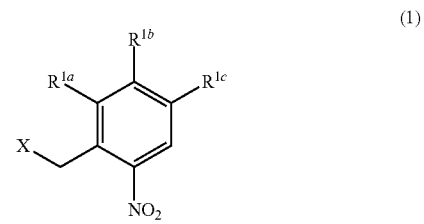

(1)

can be produced by:
a step wherein a compound represented by formula (2):

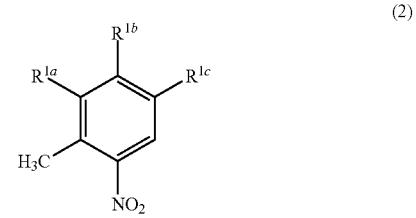

(2)

is reacted with a compound represented by formula (3):

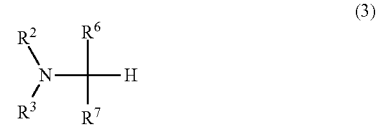

(3)

thereby obtaining a compound represented by formula (4):

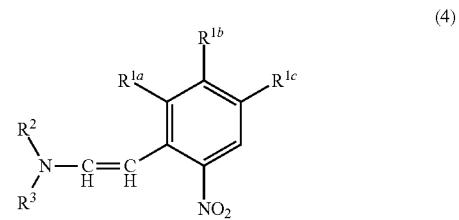

(4)

(Continued)

a step wherein a compound represented by formula (4) is reacted with hypohalogenous acid or a salt thereof, thereby obtaining a compound represented by formula (5):

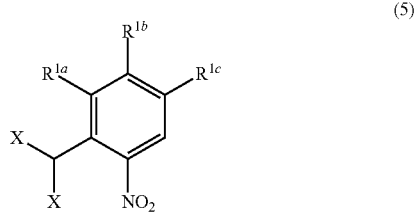

(5)

and a step wherein a compound represented by formula (5) is reduced.

11 Claims, No Drawings

(56) References Cited

FOREIGN PATENT DOCUMENTS

| WO | WO 2010/107435 A1 | 9/2010 |
| WO | WO 2013/162072 A1 | 10/2013 |

OTHER PUBLICATIONS

Makosza et al., Tele vs. oxidative substitution of hydorgen in metal monochloromethyl, dichloromethyl, and trichloromethyl nitrobenzene with Grignard reagents,.(European Journal of organic chemistry, vol. 2003, issue 19, pp. 3791-3797).*

International Preliminary Report on Patentability and Written Opinion of the International Searching Authority (Forms PCT/IB/373 and PCT/ISA/237) dated Oct. 18, 2016, for International Application No. PCT/JP2015/061526.

Eisch et. al., "Vanadium(I) Chloride and Lithium Vanadium(I) Dihydride as Selectrive Epimetallating Reagents for π- and σ-Bonded Organic Substrates", European Journal of Organic Chemistry, vol. 26, 2008, pp. 4482-4492.

International Search Report issued in PCT/JP2015/061526, dated Jul. 14, 2015.

Chinese Office Action and Search Report for Chinese Application No. 201580019624.0, dated Apr. 20, 2017, with a partial English translation of the Chinese Office Action.

* cited by examiner

METHOD FOR PRODUCING NITRO COMPOUND

TECHNICAL FIELD

The present invention relates to a method for producing a nitro compound.

BACKGROUND ART

WO2013/162072 describes a compound having a control effect on pests and shows that 2-halomethylnitrobenzene such as 2-bromomethyl-3-methylnitrobenzene can be used as a production intermediate thereof.

Further, WO2013/162072 describes that 2-bromomethyl-3-methylnitrobenzene can be produced by reacting 2-hydroxymethyl-3-methylnitrobenzene obtained from 2-methyl-6-nitrobenzoic acid, sodium borohydride and methanesulfonic acid, with boron tribromide. (Reference Production Examples 19 and 20, pages 949 to 951)

SUMMARY OF THE INVENTION

The present invention provides a method for industrially advantageously producing a compound represented by formula (1):

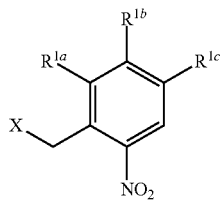
(1)

(wherein X represents a chlorine atom or a bromine atom, $R^{1a}$ represents an alkyl group having 1 to 6 carbon atoms optionally having a fluorine atom or atoms, or represents a cycloalkyl group having 3 to 6 carbon atoms, $R^{1b}$ and $R^{1c}$ independently represent an alkyl group having 1 to 6 carbon atoms optionally having a fluorine atom or atoms, a hydrogen atom or a cycloalkyl group having 3 to 6 carbon atoms).

According to the present invention, as described below, the compound represented by formula (1) can be industrially advantageously produced by a production method including the steps of reacting a compound represented by formula (2) with a compound represented by formula (3) to obtain a compound represented by formula (4), reacting the compound represented by formula (4) with a hypohalogenous acid (hypochlorous acid or hypobromous acid) or a salt thereof to obtain a compound represented by formula (5), and reducing the compound represented by formula (5) to obtain a compound represented by formula (1). Among the compounds represented by formula (4), particularly, a compound represented by formula (4') can be also produced by reacting a compound represented by formula (2) with a compound represented by formula (3) and a secondary amine represented by formula (3').

The present invention is as described below.

[1] A method for producing a compound represented by formula (1), comprising the steps of reacting a compound represented by formula (2):

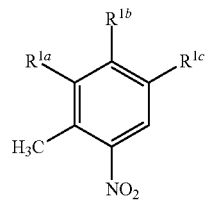
(2)

(wherein $R^{1a}$ represents an alkyl group having 1 to 6 carbon atoms optionally having a fluorine atom or atoms, or represents a cycloalkyl group having 3 to 6 carbon atoms, $R^{1b}$ and $R^{1c}$ independently represent an alkyl group having 1 to 6 carbon atoms optionally having a fluorine atom or atoms, a hydrogen atom or a cycloalkyl group having 3 to 6 carbon atoms), with a compound represented by formula (3):

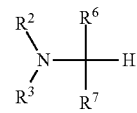
(3)

(wherein $R^2$ and $R^3$ independently represent an alkyl group having 1 to 3 carbon atoms, or $R^2$, $R^3$ and a nitrogen atom bound to $R^2$ and $R^3$ may join together to form a ring (the ring may contain an oxygen atom as a ring-constituting atom), and $R^6$ and $R^7$ independently represent an alkoxy group having 1 to 3 carbon atoms or —$NR^aR^b$, wherein $R^a$ and $R^b$ independently represent an alkyl group having 1 to 3 carbon atoms, or $R^a$, $R^b$ and a nitrogen atom bound to $R^a$ and $R^b$ may join together to form a ring, and the ring may contain an oxygen atom as a ring-constituting atom),
to obtain a compound represented by formula (4):

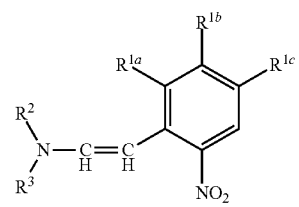
(4)

(wherein $R^{1a}$, $R^{1b}$, $R^{1c}$, $R^2$ and $R^3$ have the same meanings as described above);
reacting the compound represented by formula (4) with a hypohalogenous acid (hypochlorous acid or hypobromous acid) or a salt thereof to obtain a compound represented by formula (5):

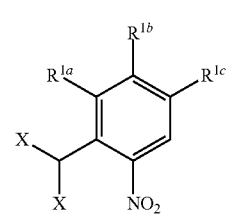
(5)

(wherein X represents a chlorine atom or a bromine atom, and $R^{1a}$, $R^{1b}$ and $R^{1c}$ have the same meanings as described above);
and reducing the compound represented by formula (5) to obtain the compound represented by formula (1):

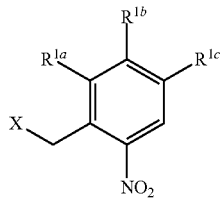

(wherein X, $R^{1a}$, $R^{1b}$ and $R^{1c}$ have the same meanings as described above).

[2] A method for producing a compound represented by formula (1), comprising the steps of reacting a compound represented by formula (2):

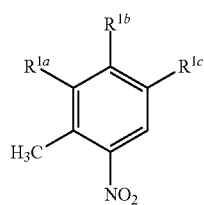

(wherein $R^{1a}$ represents an alkyl group having 1 to 6 carbon atoms optionally having a fluorine atom or atoms, or represents a cycloalkyl group having 3 to 6 carbon atoms, $R^{1b}$ and $R^{1c}$ independently represent an alkyl group having 1 to 6 carbon atoms optionally having a fluorine atom or atoms, a hydrogen atom or a cycloalkyl group having 3 to 6 carbon atoms),
with a compound represented by formula (3):

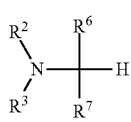

(wherein $R^2$ and $R^3$ independently represent an alkyl group having 1 to 3 carbon atoms, or $R^2$, $R^3$ and a nitrogen atom bound to $R^2$ and $R^3$ may join together to form a ring (the ring may contain an oxygen atom as a ring-constituting atom), and $R^6$ and $R^7$ independently represent an alkoxy group having 1 to 3 carbon atoms or —$NR^aR^b$, wherein $R^a$ and $R^b$ independently represent an alkyl group having 1 to 3 carbon atoms, or $R^a$, $R^b$ and a nitrogen atom bound to $R^a$ and $R^b$ may join together to form a ring, and the ring may contain an oxygen atom as a ring-constituting atom), and a secondary amine represented by formula (3'):

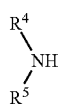

(wherein $R^4$ and $R^5$ form a ring in which $R^4$, $R^5$ and a nitrogen atom bound to $R^4$ and $R^5$ join together, and the ring may contain an oxygen atom as a ring-constituting atom), to obtain a compound represented by formula (4'):

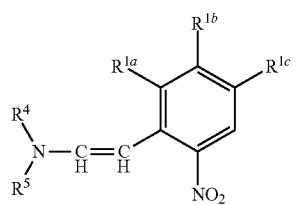

(wherein $R^{1a}$, $R^{1b}$, $R^{1c}$, $R^4$ and $R^5$ have the same meanings as described above);
reacting the compound represented by formula (4') with a hypohalogenous acid (hypochlorous acid or hypobromous acid) or a salt thereof to obtain a compound represented by formula (5):

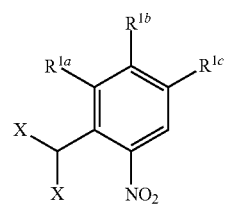

(wherein X is a chlorine atom or a bromine atom, and $R^{1a}$, $R^{1b}$ and $R^{1c}$ have the same meanings as described above);
and reducing the compound represented by formula (5) to obtain the compound represented by formula (1):

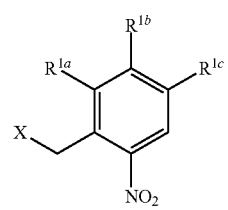

(wherein X, $R^{1a}$, $R^{1b}$ and $R^{1c}$ have the same meanings as described above).

[3] The method according to [2], wherein, in the step of reacting a compound represented by formula (2) with a compound represented by formula (3) and a secondary amine represented by formula (3') to obtain a compound represented by formula (4'), the reaction is carried out in the presence of copper iodide.

[4] The method according to any of [1] to [3], wherein, in the step of reacting the compound represented by formula (4) or formula (4') with a hypohalogenous acid or a salt thereof to obtain a compound represented by formula (5), the hypohalogenous acid or salt thereof is hypochlorous acid or a salt thereof.

[5] The method according to any of [1] to [4], wherein, in the step of reducing the compound represented by formula (5) to obtain the compound represented by formula (1), the compound represented by formula (5) is reduced in the presence of a heterogeneous platinum group catalyst and formic acid or a salt thereof.

[6] The method according to any of [1] to [5], wherein $R^{1a}$ is a methyl group, and $R^{1b}$ and $R^{1c}$ are a hydrogen atom.

[7] A nitro compound represented by formula (7):

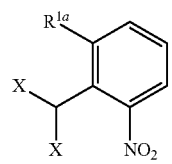

(7)

(wherein X represents a chlorine atom or a bromine atom, and $R^{1a}$ represents an alkyl group having 1 to 6 carbon atoms optionally having a fluorine atom or atoms, or a cycloalkyl group having 3 to 6 carbon atoms).

Examples of the alkyl group having 1 to 6 carbon atoms optionally having a fluorine atom or atoms in $R^{1a}$, $R^{1b}$ and $R^{1c}$ include alkyl groups such as a methyl group, an ethyl group, a propyl group, an isopropyl group, a butyl group, a sec-butyl group, a tert-butyl group, a pentyl group and a hexyl group, and alkyl groups in which one or more hydrogen atoms are substituted with a fluorine atom or atoms such as a trifluoromethyl group, a difluoromethyl group, a perfluoroethyl group, a perfluoropropyl group, a perfluoroisopropyl group, a perfluorobutyl group, a perfluoro sec-butyl group, a perfluoro tert-butyl group, a perfluoropentyl group, and a perfluorohexyl group. The alkyl group having 1 to 6 carbon atoms optionally having a fluorine atom or atoms is preferably an alkyl group having 1 to 3 carbon atoms, a trifluoromethyl group, and a difluoromethyl group.

The cycloalkyl group having 3 to 6 carbon atoms is a cyclopropyl group, a cyclobutyl group, a cyclopentyl group, or a cyclohexyl group, and the cycloalkyl group having 3 to 6 carbon atoms in $R^{1a}$, $R^{1b}$ and $R^{1c}$ is preferably a cycloalkyl group having 3 to 4 carbon atoms.

The alkyl group having 1 to 3 carbon atoms is a methyl group, an ethyl group, a propyl group or an isopropyl group, and the alkyl group having 1 to 3 carbon atoms in $R^2$, $R^3$, $R^a$ and $R^b$ is preferably a methyl group and an ethyl group.

The alkoxy group having 1 to 3 carbon atoms is a methoxy group, an ethoxy group, a propoxy group or an isopropoxy group, and the alkoxy group having 1 to 3 carbon atoms in $R^6$ and $R^7$ is preferably a methoxy group and an ethoxy group.

$R^{1a}$ is preferably an alkyl group having 1 to 3 carbon atoms, and a methyl group is more preferred.

Each of $R^{1b}$ and $R^{1c}$ is preferably a hydrogen atom.

$R^2$, $R^3$ and a nitrogen atom bound to $R^2$ and $R^3$ may join together to form a ring, and N, $R^2$ and $R^3$ may form a 5- to 7-membered ring containing a nitrogen atom. The 5- to 7-membered ring may contain an oxygen atom as a ring-constituting atom. Examples of —$NR^2R^3$ having the ring structure described above include a pyrrolidino group, a piperidino group, and a morpholino group.

Preferred —$NR^2R^3$ is a dimethylamino group, a diethylamino group, and a pyrrolidino group.

Examples of —$NR^aR^b$ include a dimethylamino group, a diethylamino group, a morpholino group, a piperidino group, and a pyrrolidino group.

$R^6$ is preferably an alkoxy group having 1 to 3 carbon atoms or —$NR^aR^b$, and a methoxy group and a dimethylamino group are more preferred.

$R^7$ is preferably an alkoxy group having 1 to 3 carbon atoms or —$NR^aR^b$, and a methoxy group and a dimethylamino group are more preferred.

$R^4$, $R^5$ and a nitrogen atom bound to $R^4$ and $R^5$ may join together to forma ring, N, $R^4$ and $R^5$ may forma 5- to 7-membered ring containing a nitrogen atom, and the 5- to 7-membered ring may contain an oxygen atom as a ring-constituting atom. Examples of —$NR^4R^5$ having the ring structure described above include a pyrrolidino group, a piperidino group, and a morpholino group.

With regard to —$NR^4R^5$, a pyrrolidino group is preferred.

First, a method for producing a compound represented by formula (4) will be described.

The compound represented by formula (4) can be produced by reacting a compound represented by formula (2) with the compound represented by formula (3).

Examples of the compound represented by formula (2) include 2,3-dimethylnitrobenzene, 2-methyl-3-ethylnitrobenzene, 2-methyl-3-cyclopropylnitrobenzene, 2-methyl-3-trifluoromethylnitrobenzene, and 2-methyl-3-difluoromethylnitrobenzene, and a commercially available one may be used, or one prepared by a known method may be used.

Examples of the compound represented by formula (3) include N,N-dimethylformamide dimethyl acetal, N,N-dimethylformamide diethyl acetal, 1-(dimethoxymethyl)pyperidine, 1-(diethoxymethyl)pyperidine, 1-(dimethoxymethyl)pyrrolidine, 1-(diethoxymethyl)pyrrolidine, 4-(dimethoxymethyl)morpholine, 4-(diethoxymethyl)morpholine, bis(N,N-dimethylamino)methoxymethane, dipiperidinomethoxymethane, dipyrrolidinomethoxymethane, dimorpholinomethoxymethane, tri(N,N-dimethylamino)methane, tripiperidinomethane, tripyrrolidinomethane, and trimorpholinomethane, and a commercially available one may be used, or one prepared by a known method may be used. Preferred compound represented by formula (3) is N,N-dimethylformamide dimethyl acetal.

The use amount of the compound represented by formula (3) is at a ratio of usually 1 to 10 mol, and preferably 1 to 3 mol, based on 1 mol of the compound represented by formula (2).

The reaction of the compound represented by formula (2) with the compound represented by formula (3) is usually carried out by mixing both compounds, and a solvent can be used in the mixing.

Examples of the solvent include hydrocarbons such as heptane, hexane, cyclohexane, pentane, toluene and xylene; ethers such as diethyl ether, tetrahydrofuran, 1,4-dioxane, ethylene glycol dimethyl ether, anisole, methyl tert-butyl ether and diisopropyl ether; halogenated hydrocarbons such as carbon tetrachloride, chloroform, dichloromethane, 1,2-dichloroethane, tetrachloroethane and chlorobenzene; nitriles such as acetonitrile and propionitrile; and mixtures thereof. The solvent is preferably N,N-dimethylformamide.

The use amount of the solvent is usually at a ratio of 0.1 to 50 parts by weight, based on 1 part by weight of the compound represented by formula (2).

The compound represented by formula (2) and the compound represented by formula (3) may be mixed at a time, or may be mixed while gradually adding either compound.

The reaction may be carried out in a nitrogen atmosphere.

The reaction temperature is within the range of usually −20 to 250° C., and preferably 50 to 200° C.

The reaction time is within the range of usually 0.1 to 72 hours, and preferably 1 to 24 hours.

The reaction mixture is concentrated, whereby the compound represented by formula (4) can be isolated. In the isolation, a solvent can be added to extract the compound, and a base may be added, as necessary.

Examples of the base include sodium hydroxide, potassium hydroxide, sodium carbonate, potassium carbonate, sodium bicarbonate, and ammonia. Examples of the solvent include ethyl acetate, benzene, toluene, xylene, hexane, heptane, chloroform, dichloromethane, diethyl ether, tert-butyl methyl ether, and water. In the case where the base is added in a form of an aqueous solution, the concentration of the base is usually 1 to 6 normal.

The isolated compound represented by formula (4) can be purified by washing, recrystallization, and the like.

Among the compounds represented by formula (4), particularly, a compound represented by formula (4') can also be produced by reacting a compound represented by formula (2) with a compound represented by formula (3) and a secondary amine represented by formula (3').

Specific examples of the compound represented by formula (2) and the compound represented by formula (3) are as described above.

Examples of the secondary amine represented by formula (3') include pyrrolidine, pyperidine, and morpholine.

The use amount of the compound represented by formula (3) is at a ratio of usually 1 to 10 mol, and preferably 1 to 3 mol, based on 1 mol of the compound represented by formula (2), and the use amount of the secondary amine represented by formula (3') is usually at a ratio of 0.05 to 10 mol, based on 1 mol of the compound represented by formula (2).

In the reaction, a copper halide may be further added together with the secondary amine, and examples of the copper halide include copper chloride, copper bromide, and copper iodide, and a monovalent copper halide is preferred. The copper halide is usually used in a ratio of 0.001 to 5 mol, based on 1 mol of the compound represented by formula (2).

The reaction of the compound represented by formula (2) with the compound represented by formula (3) and the secondary amine represented by formula (3') is usually carried out by mixing the compounds, and a solvent can be used in the mixing.

Specific examples and the use amount of the solvent are the same as those in the reaction of the compound represented by formula (2) with the compound represented by formula (3).

The mixing may be carried out under a nitrogen atmosphere.

The reaction temperature is within the range of usually −20 to 250° C., and preferably 0 to 150° C.

The reaction time is within the range of usually 0.1 to 72 hours, and preferably 1 to 24 hours.

Post treatment after completion of the reaction is the same as those in the reaction of the compound represented by formula (2) with the compound represented by formula (3).

Examples of the compounds represented by formula (4) and formula (4') include 2-{2-(N,N-dimethylamino)vinyl}-3-methylnitrobenzene, 2-{2-(N,N-diethylamino)vinyl}-3-methylnitrobenzene, 2-(2-pyrrolidinylvinyl)-3-methylnitrobenzene, 2-(2-piperidinylvinyl)-3-methylnitrobenzene, 2-(2-morpholinylvinyl)-3-methylnitrobenzene, 2-{2-(N,N-dimethylamino)vinyl}-3-ethylnitrobenzene, 2-{2-(N,N-diethylamino)vinyl}-3-ethylnitrobenzene, 2-(2-pyrrolidinylvinyl)-3-ethylnitrobenzene, 2-(2-piperidinylvinyl)-3-ethylnitrobenzene, 2-(2-morpholinylvinyl)-3-ethylnitrobenzene, 2-{2-(N,N-dimethylamino)vinyl}-3-cyclopropylnitrobenzene, 2-{2-(N,N-diethylamino)vinyl}-3-cyclopropylnitrobenzene, 2-(2-pyrrolidinylvinyl)-3-cyclopropylnitrobenzene, 2-(2-piperidinylvinyl)-3-cyclopropylnitrobenzene, 2-(2-morpholinylvinyl)-3-cyclopropylnitrobenzene, 2-{2-(N,N-dimethylamino)vinyl}-3-trifluoromethylnitrobenzene, 2-{2-(N,N-diethylamino)vinyl}-3-trifluoromethylnitrobenzene, 2-(2-pyrrolidinylvinyl)-3-trifluoromethylnitrobenzene, 2-(2-piperidinylvinyl)-3-trifluoromethylnitrobenzene, and 2-(2-morpholinylvinyl)-3-trifluoromethylnitrobenzene.

Next, a method for producing a compound represented by formula (5) will be described.

The compound represented by formula (5) can be produced by reacting the compound represented by formula (4) with a hypohalogenous acid or a salt thereof. The reaction of the compound represented by formula (4') and a hypohalogenous acid or a salt thereof can be carried out in the same manner.

In the present invention, the hypohalogenous acid refers to hypochlorous acid or hypobromous acid, and examples of the salt of hypohalogenous acid include alkali metal salts and alkaline earth metal salts of hypochlorous acid and hypobromous acid such as sodium hypochlorite, potassium hypochlorite, lithium hypochlorite, calcium hypochlorite, and sodium hypobromite. Use of alkali metal salts of hypochlorous acid is preferred, and sodium hypochlorite is more preferred.

The compound represented by formula (4) and the hypohalogenous acid or salt thereof may be mixed at a time, or may be mixed while gradually adding the hypohalogenous acid or salt thereof.

As the hypohalogenous acid or salt thereof, either a commercially available product or one produced by a known method may be used.

The use amount of the hypohalogenous acid or salt thereof is at a ratio of usually 1 to 100 mol, and preferably 1 to 10 mol, based on 1 mol of the compound represented by formula (4).

The reaction of the compound represented by formula (4) with the hypohalogenous acid or salt thereof is usually carried out by mixing both compounds in a solvent. Examples of the solvent include hydrocarbons such as heptane, hexane, cyclohexane, pentane, toluene and xylene; ethers such as diethyl ether, tetrahydrofuran, 1,4-dioxane, ethylene glycol dimethyl ether, anisole, methyl tert-butyl ether and diisopropyl ether; halogenated hydrocarbons such as carbon tetrachloride, chloroform, dichloromethane, 1,2-dichloroethane, tetrachloroethane and chlorobenzene; nitriles such as acetonitrile and propionitrile; water; and mixtures thereof. Preferred are water, acetonitrile, and toluene.

The use amount of the solvent is usually at a ratio of 0.1 to 50 parts by weight, based on 1 part by weight of the compound represented by formula (4).

In the reaction, a phase-transfer catalyst may be added, as necessary. Examples of the phase-transfer catalyst include quaternary ammonium salts such as tetramethylammonium chloride, tetraethylammonium chloride, tetrabutylammonium bromide, tetrabutylammonium chloride, tetrabutylammonium iodide, tetrabutylammonium sulfate, benzyltriethylammonium chloride and trioctylmethylammonium chloride, quaternary phosphonium salts such as tetrabutylphosphonium chloride, pyridinium compounds such as dodecylpyridinium chloride, and crown ethers. The phase-transfer catalyst is preferably a quaternary ammonium salt, and further preferably tetrabutylammonium chloride and tetrabutylammonium bromide. The use amount of the phase-transfer catalyst is usually at a ratio of 0.01 to 5 parts by weight, based on 1 part by weight of the compound represented by formula (4).

The reaction may be carried out under a nitrogen atmosphere.

The reaction temperature is within the range of usually −20 to 150° C., and preferably −10 to 100° C.

The reaction time is within the range of usually 0.1 to 72 hours, and preferably 1 to 24 hours.

The reaction mixture is concentrated, whereby the compound represented by formula (5) can be isolated. At this time, a base, salt or solvent may be added to the reaction mixture, as necessary.

Examples of the base include sodium hydroxide, potassium hydroxide, sodium carbonate, potassium carbonate, and sodium bicarbonate. Examples of the salt include sodium thiosulfate, sodium sulfite, and sodium bisulfite. Examples of the solvent include ethyl acetate, benzene, toluene, xylene, hexane, heptane, chloroform, dichloromethane, diethyl ether, tert-butyl methyl ether, and water. In the case where a base or salt is added in a form of an aqueous solution, the concentration of the base is usually 1 to 6 normal, and the concentration of the salt is usually 1 to 6 mol/L. The amount of the solvent to be added is usually at a ratio of 1 to 50 parts by weight, based on 1 part by weight of the compound represented by formula (5).

The isolated compound represented by formula (5) can be purified by washing, column chromatography, and the like.

Examples of the compound represented by formula (5) include 2-dichloromethyl-3-methylnitrobenzene, 2-dibromomethyl-3-methylnitrobenzene, 2-dichloromethyl-3-ethylnitrobenzene, 2-dibromomethyl-3-ethylnitrobenzene, 2-dichloromethyl-3-cyclopropylnitrobenzene, 2-dibromomethyl-3-cyclopropylnitrobenzene, 2-dichloromethyl-3-trifluoromethylnitrobenzene, and 2-dibromomethyl-3-trifluoromethylnitrobenzene.

Subsequently, a method for producing a compound represented by formula (1) from the compound represented by formula (5) will be described.

The compound represented by formula (1) can be produced by reacting the compound represented by formula (5) with a reducing agent, in the presence of a catalyst.

Examples of the reducing agent include hydrogen; formic acid; formates such as ammonium formate, sodium formate and potassium formate; and boron compounds such as lithium triethylborohydride, diisobutylaluminum hydride, lithium aminoborohydride, lithium borohydride, sodium borohydride, borane, borane dimethyl sulfide complex and borane tetrahydrofuran complex; and formic acid and salts thereof are preferred, and alkali metal salts of formic acid such as sodium formate and potassium formate and ammonium formate are more preferred.

The reducing agent is usually used in a ratio of 0.05 to 50 mol, based on 1 mol of the compound represented by formula (5).

Examples of the catalyst are heterogeneous platinum group catalysts such as palladium-supported carbon (Pd/C), platinum-supported carbon (Pt/C), osmium-supported carbon (Os/C), ruthenium-supported carbon (Ru/C) and rhodium-supported carbon (Rh/C) and nickel catalysts such as Raney nickel and nickel chloride, and palladium-supported carbon is preferred. Platinum group herein refers to palladium, platinum, ruthenium, rhodium, iridium, and osmium.

The catalyst is usually used in a ratio of 0.05 to 3 mol, based on 1 mol of the compound represented by formula (5).

The compound represented by formula (5) and the reducing agent may be mixed at a time, or may be mixed while gradually adding the reducing agent.

The reaction is usually carried out in a solvent. Examples of the solvent include alcohols such as methanol, ethanol, propanol and butanol; esters such as ethyl acetate and butyl acetate; ethers such as diethyl ether, tetrahydrofuran, 1,4-dioxane, ethylene glycol dimethyl ether, anisole, methyl tert-butyl ether and diisopropyl ether; hydrocarbons such as heptane, hexane, cyclohexane, pentane, toluene and xylene; water; and mixtures thereof.

The use amount of the solvent is usually in a ratio of 0.1 to 50 parts by weight, based on 1 part by weight of the compound represented by formula (5).

The reaction temperature is usually within the range of 0 to 100° C.

The reaction time is usually within the range of 0.1 to 72 hours.

EXAMPLES

The present invention will be described in further detail below by way of Examples.

Example 1

A mixture of 30 g of 2,3-dimethylnitrobenzene, 39.5 g of N,N-dimethylforamide dimethylacetal and 200 mL of N,N-dimethylforamide was heated at 175° C. for 10 hours. The reaction mixture was concentrated to obtain 38.0 g of 2-{2-(N,N-dimethylamino)vinyl}-3-methylnitrobenzene.

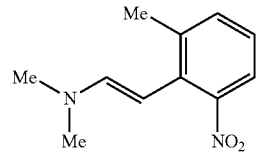

$^1$H-NMR (CDCl$_3$) δ (ppm): 2.37 (3H, s), 2.79 (6H, s), 5.01 (1H, d, J=14.0 Hz), 6.29 (1H, d, J=14.0 Hz), 7.01 (1H, t, J=7.8 Hz), 7.27 (1H, d, J=7.2 Hz), 7.37 (1H, d, J=8.2 Hz)

Example 2

A mixture of 10 g of 2,3-dimethylnitrobenzene, 15.8 g of N,N-dimethylforamide dimethylacetal, 27.2 mL of pyrrolidine and 1.26 g of copper(I) iodide was heated at 100° C. for 10 hours. According to $^1$H-NMR measurement of the reaction mixture, it was confirmed that 2-(2-pyrrolidinylvinyl)-3-methylnitrobenzene was obtained in a yield of 97%.

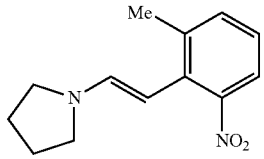 [SMILES: Cc1cccc([N+](=O)[O-])c1/C=C/N1CCCC1]

$^1$H-NMR (CDCl$_3$) δ (ppm): 1.89-1.95 (4H, m), 2.37 (3H, s), 3.20-3.24 (4H, m), 4.95 (1H, d, J=13.8 Hz), 6.62 (1H, d, J=13.8 Hz), 6.96 (1H, t, J=7.8 Hz), 7.25 (1H, d, J=7.5 Hz), 7.36 (1H, d, J=7.9 Hz)

Example 3

A mixture of 10 g of 2,3-dimethylnitrobenzene, 15.8 g of N,N-dimethylforamide dimethylacetal and 27.2 mL of pyrrolidine was heated at 100° C. for 10 hours. According to $^1$H-NMR measurement of the reaction mixture, it was confirmed that 2-(2-pyrrolidinylvinyl)-3-methylnitrobenzene was obtained in a yield of 40%.

Example 4

A mixture of 60 g of 2-(2-pyrrolidinylvinyl)-3-methylnitrobenzene, 1590 g of an aqueous sodium hypochlorite solution (concentration of about 5%) and 530 mL of acetonitrile was stirred at 0° C. for 1 hour. A saturated aqueous sodium bicarbonate solution was added to the reaction mixture, and extraction was performed with toluene. The organic layer was washed with a saturated aqueous sodium bicarbonate solution, and dried over anhydrous sodium sulfate, then concentrated under reduced pressure to obtain 43.7 g of 2-dichloromethyl-3-methylnitrobenzene.

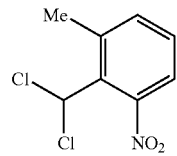

$^1$H-NMR (CDCl$_3$) δ (ppm): 2.85 (3H, s), 7.27 (1H, s), 7.42 (1H, t, J=7.9 Hz), 7.51 (1H, d, J=7.6 Hz), 7.60 (1H, dd, J=8.0, 0.9 Hz)

Example 5

A mixture of 6.2 g of 2-{2-(N,N-dimethylamino)vinyl}-3-methylnitrobenzene, 7 ml of toluene, 3.5 g of water and 0.49 g of tetrabutylammonium bromide was stirred at 0° C. To the reaction mixture, 81 g of an aqueous 10% hypochlorous acid solution was added dropwise, and the mixture was stirred at 0° C. for 1 hour, then heated to 15° C., and further stirred for 3 hours. Subsequently, the organic layer was isolated, and sequentially washed with 7 g of a saturated aqueous sodium bisulfite solution and 7 g of water, then concentrated to obtain 4.0 g of 2-dichloromethyl-3-methylnitrobenzene.

Example 6

A mixture of 10 g of 2-dichloromethyl-3-methylnitrobenzene, 0.24 g of palladium-supported carbon (10%), 49.5 g of sodium formate, 50 mL of ethylene glycol dimethyl ether and 50 mL of water was stirred at room temperature for 7 hours. Saturated saline was added to the reaction mixture, and extraction was performed with ethyl acetate. The organic layer was washed with a saturated aqueous sodium bicarbonate solution, and dried over anhydrous sodium sulfate, then concentrated under reduced pressure to obtain 7.7 g of a product. As a result of $^1$H-NMR measurement, it was confirmed that 2-chloromethyl-3-methylnitrobenzene (yield 81%) was obtained.

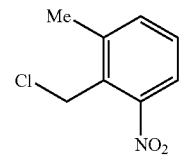

$^1$H-NMR (CDCl$_3$) δ (ppm): 2.56 (3H, s), 4.82 (2H, s), 7.39 (1H, t, J=7.9 Hz), 7.48 (1H, d, J=7.5 Hz), 7.74 (1H, d, J=8.2 Hz)

Example 7

A mixture of 150 mg of 2-dichloromethyl-3-methylnitrobenzene, 0.1 g of palladium-supported carbon (5%), 0.65 g of ammonium formate, 0.6 g of ethylene glycol dimethyl ether and 0.6 g of water was stirred at room temperature for 4 hours. The reaction mixture was diluted with 10 g of toluene, and filtered using Celite (registered trademark). The organic layer obtained by washing the filtrate with 5 g of saturated saline was concentrated to obtain 95 mg of 2-chloromethyl-3-methylnitrobenzene.

INDUSTRIAL APPLICABILITY

According to the present invention, a compound represented by formula (1) useful as a production intermediate of a compound having a control effect on pests can be industrially advantageously produced.

The invention claimed is:

1. A method for producing a compound of formula (1), comprising the steps of reacting a compound of the following formula (2):

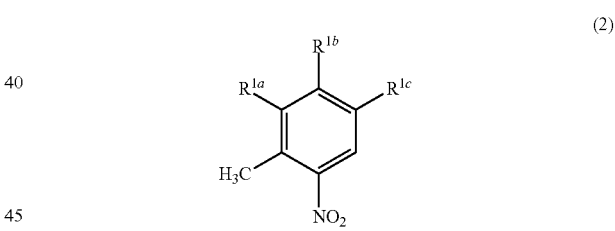

wherein $R^{1a}$ represents an alkyl group having 1 to 6 carbon atoms optionally having a fluorine atom or atoms, or represents a cycloalkyl group having 3 to 6 carbon atoms, $R^{1b}$ and $R^{1c}$ independently represent an alkyl group having 1 to 6 carbon atoms optionally having a fluorine atom or atoms, a hydrogen atom or a cycloalkyl group having 3 to 6 carbon atoms, with a compound of the following formula (3):

wherein $R^2$ and $R^3$ independently represent an alkyl group having 1 to 3 carbon atoms, or $R^2$, $R^3$ and a nitrogen atom bound to $R^2$ and $R^3$ may join together to form a ring, and the ring may contain an oxygen atom as a ring-constituting atom, and $R^6$ and $R^7$ independently represent an alkoxy group having 1 to 3 carbon atoms or —$NR^aR^b$, wherein $R^a$ and $R^b$ independently represent an alkyl group having 1 to 3 carbon atoms, or $R^a$, $R^b$ and a nitrogen atom bound to $R^a$ and $R^b$ may join together to form a ring, and the ring may contain an oxygen atom as a ring-constituting atom, to obtain a compound of the following formula (4):

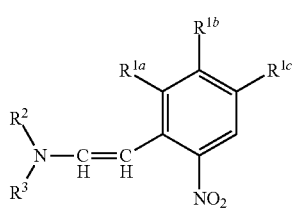
(4)

wherein $R^{1a}$, $R^{1b}$, $R^{1c}$, $R^2$ and $R^3$ have the same meanings as described above;

reacting the compound of formula (4) with a hypohalogenous acid or a salt thereof to obtain a compound of the following formula (5):

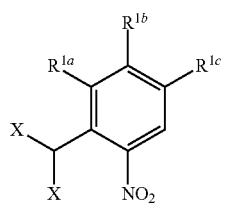
(5)

wherein X is a chlorine atom or a bromine atom, and $R^{1a}$, $R^{1b}$ and $R^{1c}$ represent the same meanings as described above;

and reducing the compound of formula (5) to obtain the compound of formula (1):

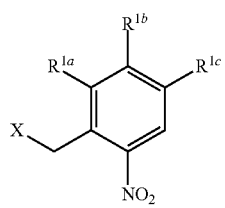
(1)

wherein X, $R^{1a}$, $R^{1b}$ and $R^{1c}$ have the same meanings as described above.

2. A method for producing a compound of formula (1), comprising the steps of reacting a compound of the following formula (2):

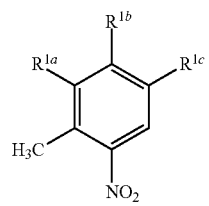
(2)

wherein $R^{1a}$ represents an alkyl group having 1 to 6 carbon atoms optionally having a fluorine atom or atoms, or represents a cycloalkyl group having 3 to 6 carbon atoms, $R^{1b}$ and $R^{1c}$ independently represent an alkyl group having 1 to 6 carbon atoms optionally having a fluorine atom or atoms, a hydrogen atom or a cycloalkyl group having 3 to 6 carbon atoms, with a compound of the following formula (3):

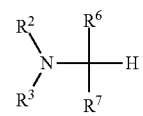
(3)

wherein $R^2$ and $R^3$ independently represent an alkyl group having 1 to 3 carbon atoms, or $R^2$, $R^3$ and a nitrogen atom bound to $R^2$ and $R^3$ may join together to form a ring, and the ring may contain an oxygen atom as a ring-constituting atom, and $R^6$ and $R^7$ independently represent an alkoxy group having 1 to 3 carbon atoms or —$NR^aR^b$, wherein $R^a$ and $R^b$ independently represent an alkyl group having 1 to 3 carbon atoms, or $R^a$, $R^b$ and a nitrogen atom bound to $R^a$ and $R^b$ may join together to form a ring, and the ring may contain an oxygen atom as a ring-constituting atom, and a secondary amine of the following formula (3'):

(3')

wherein $R^4$ and $R^5$ form a ring in which $R^4$, $R^5$ and a nitrogen atom bound to $R^4$ and $R^5$ join together, and the ring may contain an oxygen atom as a ring-constituting atom, to obtain a compound of the following formula (4'):

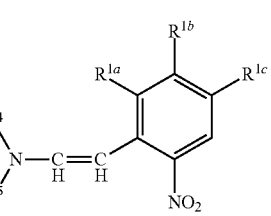
(4')

wherein $R^{1a}$, $R^{1b}$, $R^{1c}$, $R^4$ and $R^5$ have the same meanings as described above;

reacting the compound of formula (4') with a hypohalogenous acid or a salt thereof to obtain a compound of the following formula (5):

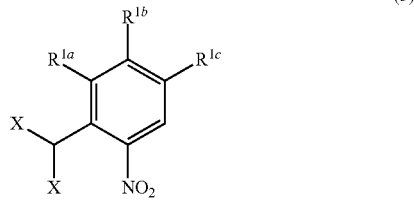

(5)

wherein X is a chlorine atom or a bromine atom, and $R^{1a}$, $R^{1b}$ and $R^{1c}$ have the same meanings as described above;

and reducing the compound of formula (5) to obtain the compound of formula (1):

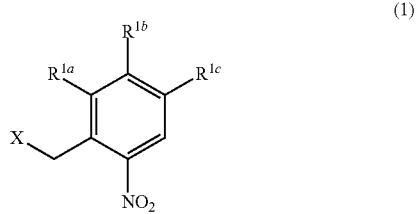

(1)

wherein X, $R^{1a}$, $R^{1b}$ and $R^{1c}$ have the same meanings as described above.

3. The method according to claim 2, wherein, in the step of reacting a compound of formula (2) with a compound of formula (3) and a secondary amine of formula (3') to obtain a compound of formula (4'), the reaction is carried out in the presence of copper iodide.

4. The method according to claim 2, wherein the secondary amine is pyrrolidine.

5. The method according to claim 1, wherein, in the step of reacting the compound of formula (4) with a hypohalogenous acid or a salt thereof to obtain a compound of formula (5), the hypohalogenous acid or salt thereof is hypochlorous acid or a salt thereof.

6. The method according to claim 2, wherein, in the step of reacting the compound of formula (4') with a hypohalogenous acid or a salt thereof to obtain a compound of formula (5), the hypohalogenous acid or salt thereof is hypochlorous acid or a salt thereof.

7. The method according to claim 1, wherein, in the step of reducing the compound of formula (5) to obtain the compound of formula (1), the compound of formula (5) is reduced in the presence of a heterogeneous platinum group catalyst and formic acid or a salt thereof.

8. The method according to claim 2, wherein, in the step of reducing the compound of formula (5) to obtain the compound of formula (1), the compound of formula (5) is reduced in the presence of a heterogeneous platinum group catalyst and formic acid or a salt thereof.

9. The method according to claim 1, wherein $R^{1a}$ is a methyl group, and $R^{1b}$ and $R^{1c}$ are a hydrogen atom.

10. The method according to claim 2, wherein $R^{1a}$ is a methyl group, and $R^{1b}$ and $R^{1c}$ are a hydrogen atom.

11. A nitro compound of the following formula (7):

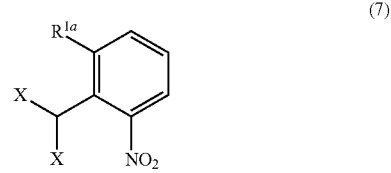

(7)

wherein X represents a chlorine atom or a bromine atom, and $R^{1a}$ represents an alkyl group having 1 to 6 carbon atoms optionally having a fluorine atom or atoms, or a cycloalkyl group having 3 to 6 carbon atoms.

* * * * *